United States Patent [19]

Green et al.

[11] Patent Number: 4,802,614

[45] Date of Patent: Feb. 7, 1989

[54] SURGICAL STAPLING INSTRUMENT AND CARTRIDGE

[75] Inventors: David T. Green, Norwalk; Henry R. Sienkiewicz, Stamford, both of Conn.

[73] Assignee: United States Surgical Corporation, Norwalk, Conn.

[21] Appl. No.: 866,800

[22] Filed: May 23, 1986

[51] Int. Cl.[4] .............................................. A61B 17/00
[52] U.S. Cl. ............................... 227/19; 227/DIG. 1
[58] Field of Search ............. 728/334 R; 227/DIG. 1, 227/19

[56] References Cited

U.S. PATENT DOCUMENTS

| | | | |
|---|---|---|---|
| 3,252,643 | 5/1966 | Strekopytov et al. | 227/DIG. 1 |
| 3,275,211 | 9/1966 | Hirsch et al. | 227/DIG. 1 |
| 3,494,533 | 2/1970 | Green et al. | 227/DIG. 1 |
| 3,795,034 | 3/1974 | Strekopytov et al. | 227/DIG. 1 |
| 4,383,634 | 5/1983 | Green | 227/DIG. 1 |
| 4,402,444 | 9/1983 | Green | 227/DIG. 1 |
| 4,520,817 | 6/1985 | Green | 227/DIG. 1 |
| 4,606,345 | 8/1986 | Dorband et al. | 227/DIG. 1 |

*Primary Examiner*—Paul A. Bell
*Attorney, Agent, or Firm*—Kenyon & Kenyon

[57] ABSTRACT

The surgical stapling instrument is provided with an integral cartridge holders as well as a retaining pin and recess which serves to align the cartridge holder relative to the anvil while retaining the distal actuator bar from pivoting into an open position. In addition, the stapling cartridge is provided with four rows of staggered staples in order to provide a stapled seam through which blood is precluded from flowing.

8 Claims, 6 Drawing Sheets

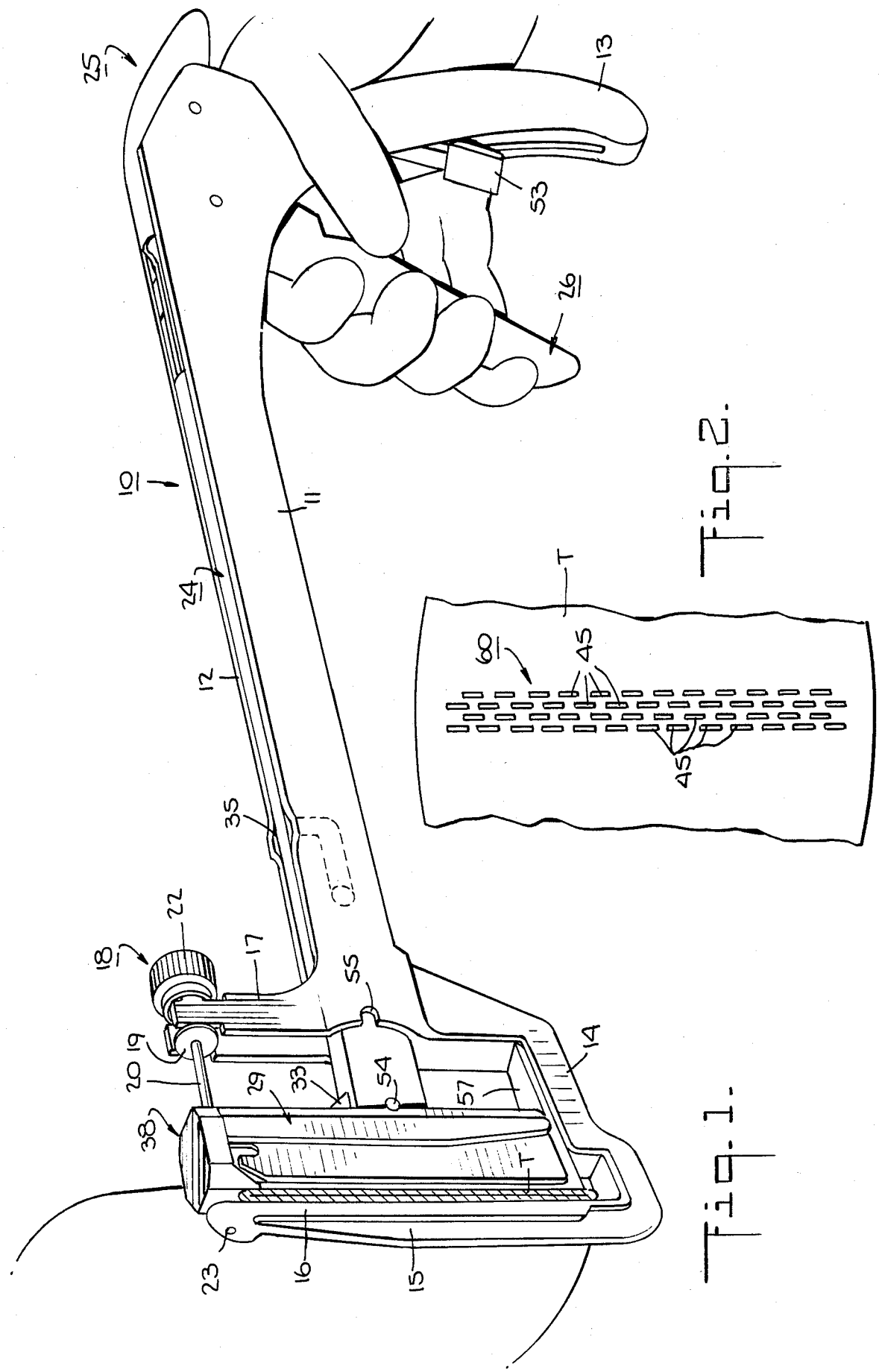

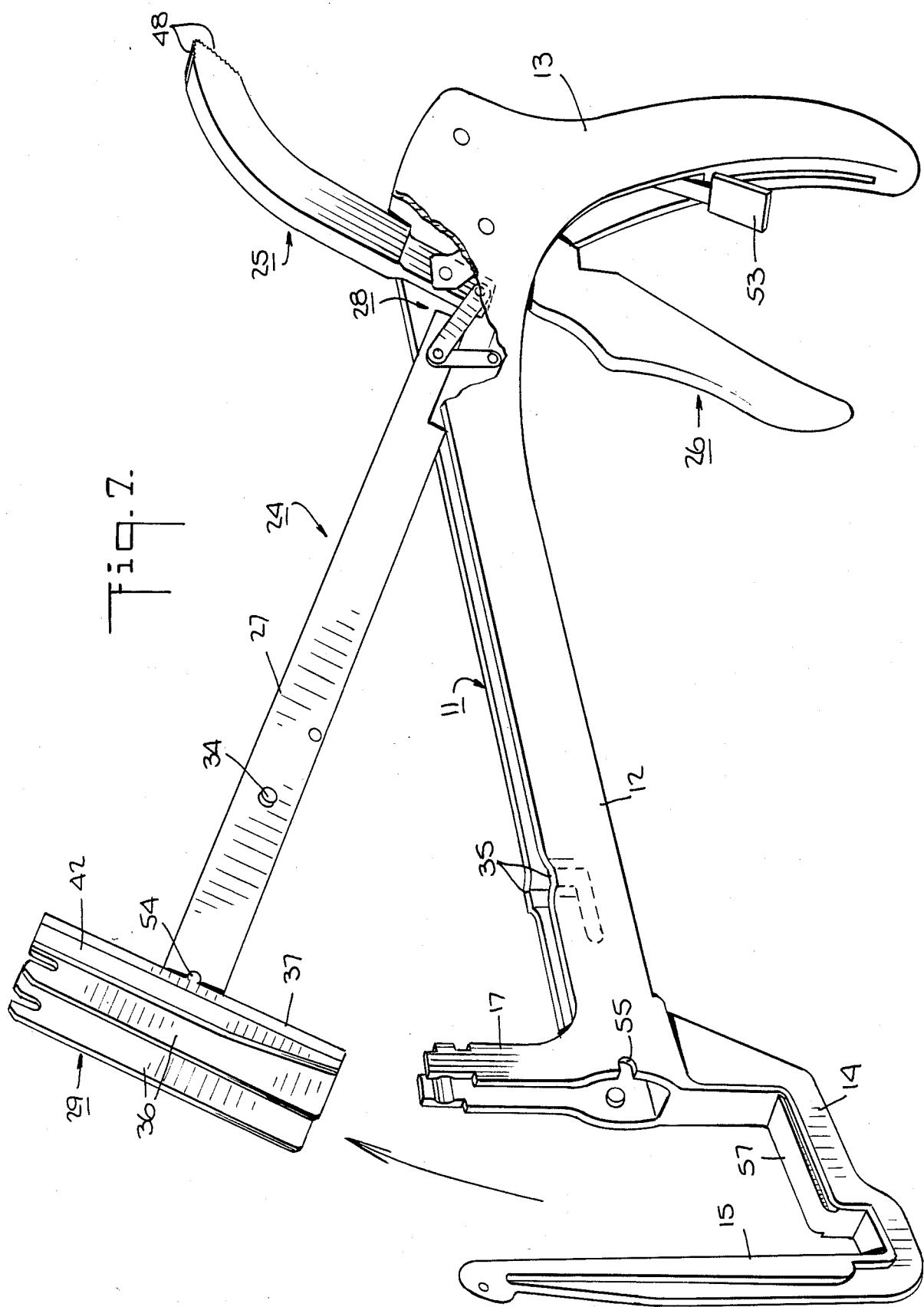

SURGICAL STAPLING INSTRUMENT AND CARTRIDGE

This invention relates to a surgical stapling instrument and a cartridge. More particularly, this invention relates to a bariatric instrument. Still more particularly, this invention relates to a stapling cartridge.

Heretofore, various types of surgical stapling instruments have been known for applying surgical fasteners such as surgical staples. In some cases, as described in U.S. Pat. No. 3,275,211, the instruments have been constructed to receive a stapling cartridges from which staples can be expelled by the operation of an actuator control elements of the instrument. In other cases, cartridges have been constructed so as to have a self-contained anvil against which the staples can be expelled by a suitable actuating mechanism. Generally, it is required that the cartridge fit snuly in a holder and that the holder be precisely aligned with the anvil while at the same time being movable relative to the anvil.

Surgical stapling instruments have been known, for example from U.S. Pat. No. 4,383,634, to be constructed with actuating means which can be pivoted out of a frame in order to permit cleaning of the various actuator elements and the frame after use. In such constructions, the frame of the instrument has been constructed to receive a cartridge having an anvil attached thereto and which is constructed to cooperate with a reciprocable actuator means of the instrument in order to expel the staples during a translation movement. Thus, in these cases, care must be taken that the cartridge is properly aligned in the frame prior to performing a stapling operation.

It has also been known that problems arise in the case of bariatric patients where stapling of a stomach has taken place. Specifically, it has been found when the stomach of a bariatric patient has been stapled, for example to reduce the food-receiving portion of the stomach by about one-half, two rows of staples have usually been used to form a seam to block the flow of food into the closed-off portion of the stomach. However, should a patient intake a relatively large amount of food, a risk exists that the stapled seam is disrupted. That is, sufficient pressure may be placed on a staple as to cause the staple to pull out of the seam. Should this occur, a zipper-like effect occurs on the row of staples so that the entire row pulls out. The same effect may then occur in the remaining row of staples. In order to overcome this problem, it has been known to use two stapling instruments one after the other to form a reinforced stapled seam. In this case, after one instrument forms a seam of two rows of staples in the patient, the second instrument is then placed adjacent to the seam to add two additional rows of staples. However, if the rows of staples are placed too close to each other, a risk arises that one row of staples may become superimposed on a stapled row so that mis-firing or jamming of the second instrument may occur. Further, if the rows of staples are placed too close together, the blood flow through the tissue may be cut off. In the event that the two pairs of rows of staples are placed too far apart, the zipper effect remains. Further, the tissue between the two sets of staple rows may not receive sufficient blood so that the tissue becomes necrotic. As is known, any strip of necrotic tissue in the stomach can become a major problem.

Accordingly, it is an object of the invention to provide a stapled seam in the tissue of a patient which is not subject to disruption.

It is another object of the invention to be able to form a stapled seam in a bariatric patient in a rapid efficient manner.

It is another object of the invention to provide a surgical stapling instrument which can be readily cleaned after use while providing precise alignment for a stapling cartridge mounted in the instrument during use.

It is another object of the invention to provide a surgical stapling instrument of relatively simple construction which provides for proper alignment of a disposable stapling cartridge relative to an anvil of the instrument.

Briefly, the invention provides a stapling cartridge which is comprised of a housing having four parallel rows of apertures on a distal side which are disposed in a staggered arrangement and through which staples disposed in alignment with the apertures may be expelled from within the housing. In addition, the cartridge has a suitable means within the housing for moving the staples simultaneously from within the housing through the apertures under a pushing force applied through an opening in a proximal side of the housing. The rows of apertures of the housing are arranged in closely spaced relation, for example on a centerline-to-centerline spacing of 0.08 inches. The staggering and spacing of the apertures of the rows provide a pattern which produces a stapled seam in the tissue, for example in a bariatric patient, which is resistant to disruption. Further, the apertures are positioned so that a tortuous path through the resultant stapled seam is created.

The invention also provides a method of stapling tissue which comprises the steps of placing the tissue within a surgical stapling instrument and driving at least four parallel staggered and closely spaced rows of surgical staples through the tissue in order to define a seam which is characterized in being resistant to disruption.

The invention also provides a surgical stapling instrument which can be readily cleaned after use and which provides for alignment of disposable stapling cartridges. To this end, the instrument includes a frame which has an anvil disposed at a distal end and a first actuator means connected at a proximal end to the frame for movement between a closed position coaxial with the frame and an open position away from the frame in order to permit cleaning of the frame and actuator means. In addition, this actuator means is reciprocally mounted within the frame when in the closed position. The instrument also has a stapling cartridge holder integrally mounted on a distal end of the actuator means and a second actuator means connected to the frame and the first actuator means for movement between an open position away from the frame and a closed position within the frame for reciprocating the first actuator means within the frame when in the closed position thereof.

The cartridge holder being integral with the first actuator means permits ready alignment of a cartridge received within the holder relative to the first actuator means. At the same time, the holder may be cleaned with the remainder of the first actuator means.

The stapling instrument also includes a retaining means for retaining the first actuator means in the frame when in the closed position in order to prevent movement of the first actuator means to the open position.

For example, the retaining means may include a pin on the first actuator means adjacent the cartridge holder and a recess in the frame for receiving the pin therein.

The instrument also includes a plunger rod which is reciprocally mounted in the first actuator means for expelling staples from a cartridge mounted in the holder. This plunger is aligned with the second actuator means in order to be moved by the second actuator means, for example, by a handle pivotally mounted in the frame, in order to expel staples from a cartridge in the holder against the anvil.

The construction of the anvil mirrors the pattern of apertures in a stapling cartridge which is to be mounted in the cartridge holder so as to effect stapling of tissue.

When the instrument is to be used, for example, for bariatric stapling, the second actuator means is pivoted to the open position while the first actuator means is disposed in a closed position relative to the frame. At this time, the pin of the retaining means is disposed in the recess provided for the pin in the frame so that the first actuator means cannot pivot from the frame into an open position. Next, a stapling cartridge is inserted into the cartridge holder if not previously inserted. Thereafter, the tissue to be stapled is positioned between the anvil and the stapling cartridge. A suitable alignment and guide pin, as is known, is then passed through the cartridge and the frame so that the cartridge may be guided between the pin and, for example, a runner or rail on the frame at an opposite end of the cartridge.

The second actuator assembly is then pivoted into a closed position. This causes the first actuator means and the cartridge holder to move so as to clamp the tissue to be stapled between the anvil and the base of the stapling cartridge. Next, the handle is then pivoted to cause the plunger rod to expel the staples through the tissue and against the anvil to form a stapled seam within the tissue.

These and other objects and advantages of the invention will become more apparent from the following detailed description taken in conjunction with the accompanying drawings wherein:

FIG. 1 illustrates a perspective view of a surgical stapling instrument in accordance with the invention;

FIG. 2 illustrates a plan view of a stapled seam in the tissue of a bariatric patient in accordance with the invention;

FIG. 7 illustrates a view of the surgical instrument in an open position for cleaning purposes.

Figure 3:
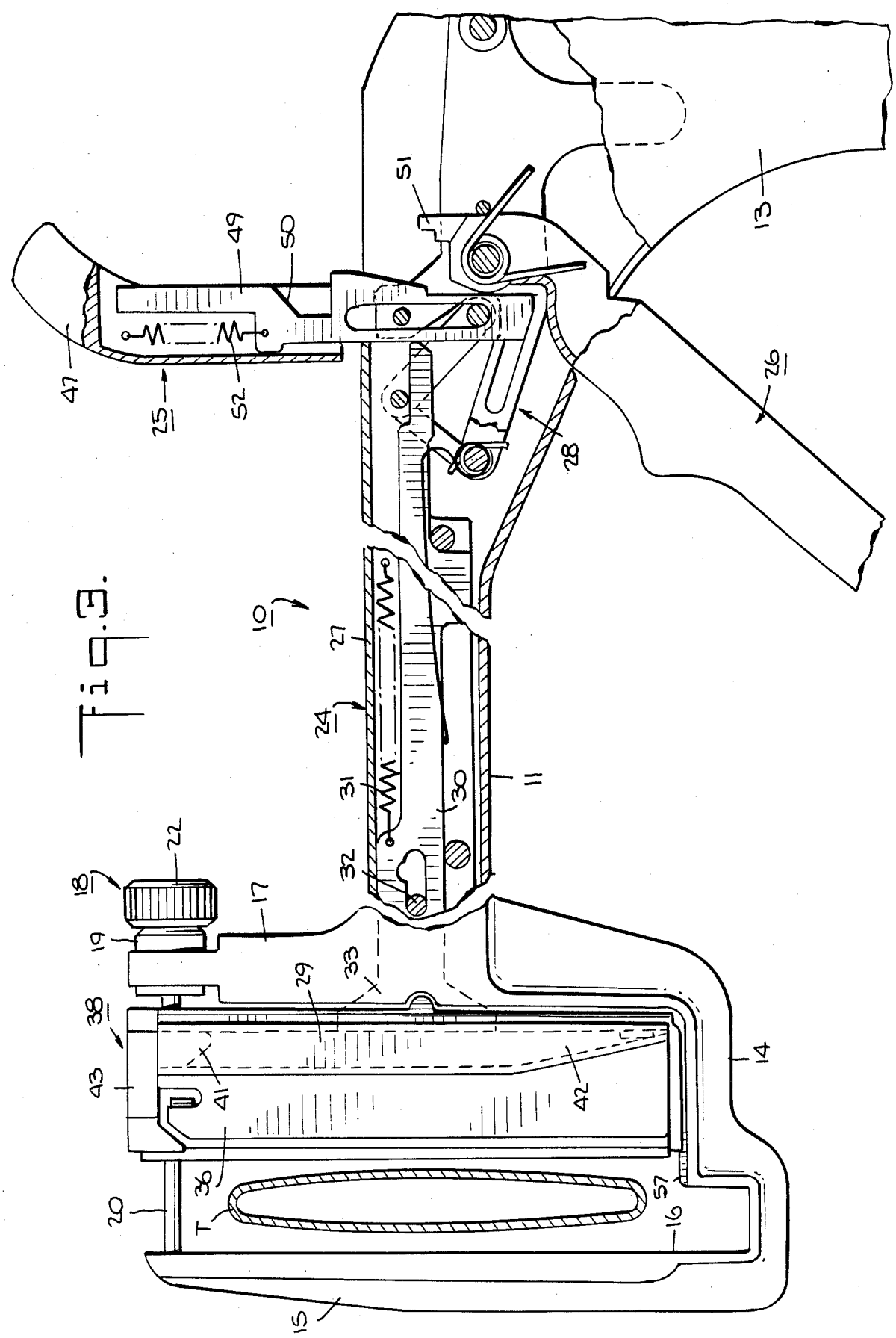
FIG. 3 illustrates the instrument of FIG. 1 in an initial position about the tissue which is to be stapled.

Referring to FIG. 1, the surgical stapling instrument 10 is constructed, for example for use in the bariatric treatment of obese patients. In this regard, the instrument 10 includes a frame 11 which defines an elongated channel-shaped portion 12, a hand grip portion 13 at the proximal end and a U-shaped extension 14 at the distal end. This U-shaped extension 14 includes a distal leg 15 on which an anvil 16 is integrally formed. In addition, the frame includes a cleft 17 formed by a pair of outstanding arms for receiving an alignment and guide pin unit 18.

Figure 6:
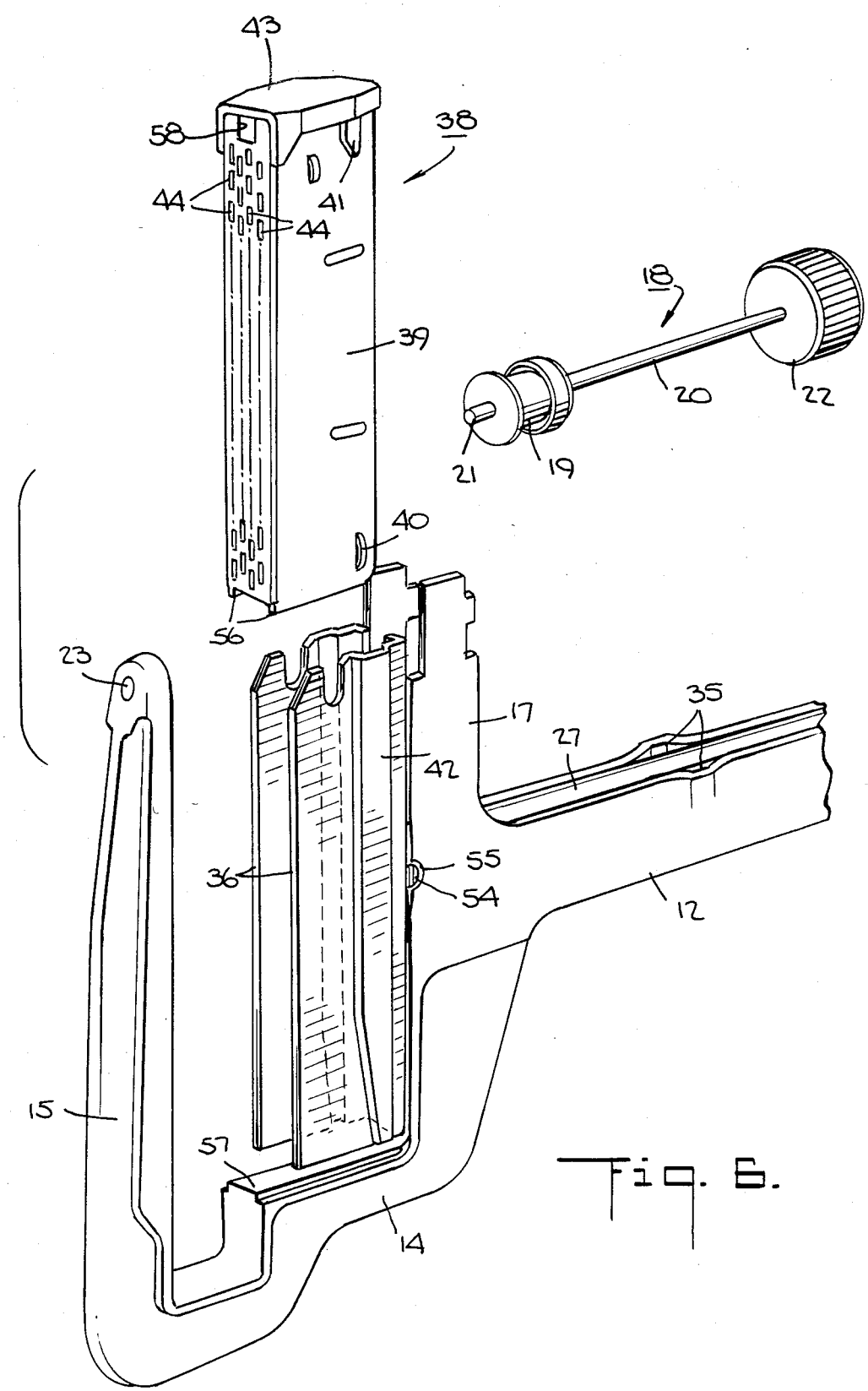
FIG. 6 illustrates an exploded view of a stapling cartridge, alignment pin and distal end of the surgical instrument.

Referring to FIG. 6, the alignment and guide pin unit 18 is of generally known construction and includes a tubular collar 19 which can be snap fitted in place between the arms of the cleft 17 while being freely rotatable therein. In addition, the unit 18 includes a pin 20 which is slidable within the collar 19 and which has a threaded distal end 21 and carries a knurled knob 22 at the proximal end. The pin 20 also has a circumferential recess (not shown) near the threaded end which receives a spring clip (not shown) which is internally mounted in the collar 19. Thus, the pin 20 can be retained in a fixed position when the collar 19 is inserted in the cleft 17 until the surgeon is ready to move the pin 20 forward as described below. The threaded distal end 21 cooperates with a threaded aperture 23 in the distal leg 15 of the U-shaped extension 14 of the frame 11 when the pin 20 is moved forward.

Referring to FIG. 7, the instrument 10 includes a pair of actuator means 24, 25 and a handle 26 which are articulated within the frame 11 for movement relative to and with each other.

The first or distal actuator means 24 is connected at the proximal end to the frame 11 for movement between a closed position as shown in FIG. 1 coaxial with the frame 11 and an open position as shown in FIG. 7 away from the frame 11 in order to permit cleaning. The distal actuator means 24 includes an elongated channel shaped bar 27 which is articulated by a joint 28 at the proximal end to the frame 11 and proximal actuator means 25 and which carries a stapling cartridge holder 29 which is integrally mounted at the distal end. In addition, a plunger rod 30 is disposed internally of the channel shaped bar 27 as shown in FIG. 3. This plunger rod 30 is biased by a spring 31 in the proximal direction against a stop pin 32 which is fixed within the bar 27. As indicated in FIG. 3, the plunger rod 30 has an enlarged head 33 which extends into an opening at the proximal end of the cartridge holder 29.

The channel shaped bar 27 also carries a pin 34 which extends on opposite sides for reception within L-shaped guide slots 35 in the frame as indicated in FIG. 7.

The cartridge holder 29 is formed of a U-shaped member having a pair of arms 36 and a base 37 which is secured as by welding to the channel shaped bar 27. As indicated in FIG. 6, a stapling cartridge 38 includes a housing 39 which has outstanding tabs 40, 41 which are received in elongated guide recesses 42 of the arms 36 of the holder 29. As indicated, each guide recess 42 tapers to a narrowed section at a forward end to receive tabs 40 of relatively small size while the rear ends of the recesses 42 receive enlarged tabs 41, for example of plastic, which are provided on an end cap 43 of the cartridge 38. Thus, the tabs 40, 41 serve to align the cartridge 38 within the holder 29.

The cartridge 38 also includes four parallel rows 44 of apertures on a distal side which are disposed in staggered arrangement as well as in a closely spaced relation, for example on a centerline-to-centerline spacing of 0.08 inches.

The cartridge 38 also includes a plurality of staples 45 (see FIG. 4) which are disposed within the housing 39 in known manner. In this regard, a means, for example in the form of a pusher bar 46 (see FIG. 4) is disposed in the housing 39 in order to move the staples 45 through the apertures 44. To this end, a suitable opening (not shown) is provided in the proximal side of the housing 39 so as to permit entry of the enlarged head 33 of the plunger rod 30.

The anvil 16 of the frame 11 is also provided with matching recesses for the apertures 44 in known manner.

Figure 4:
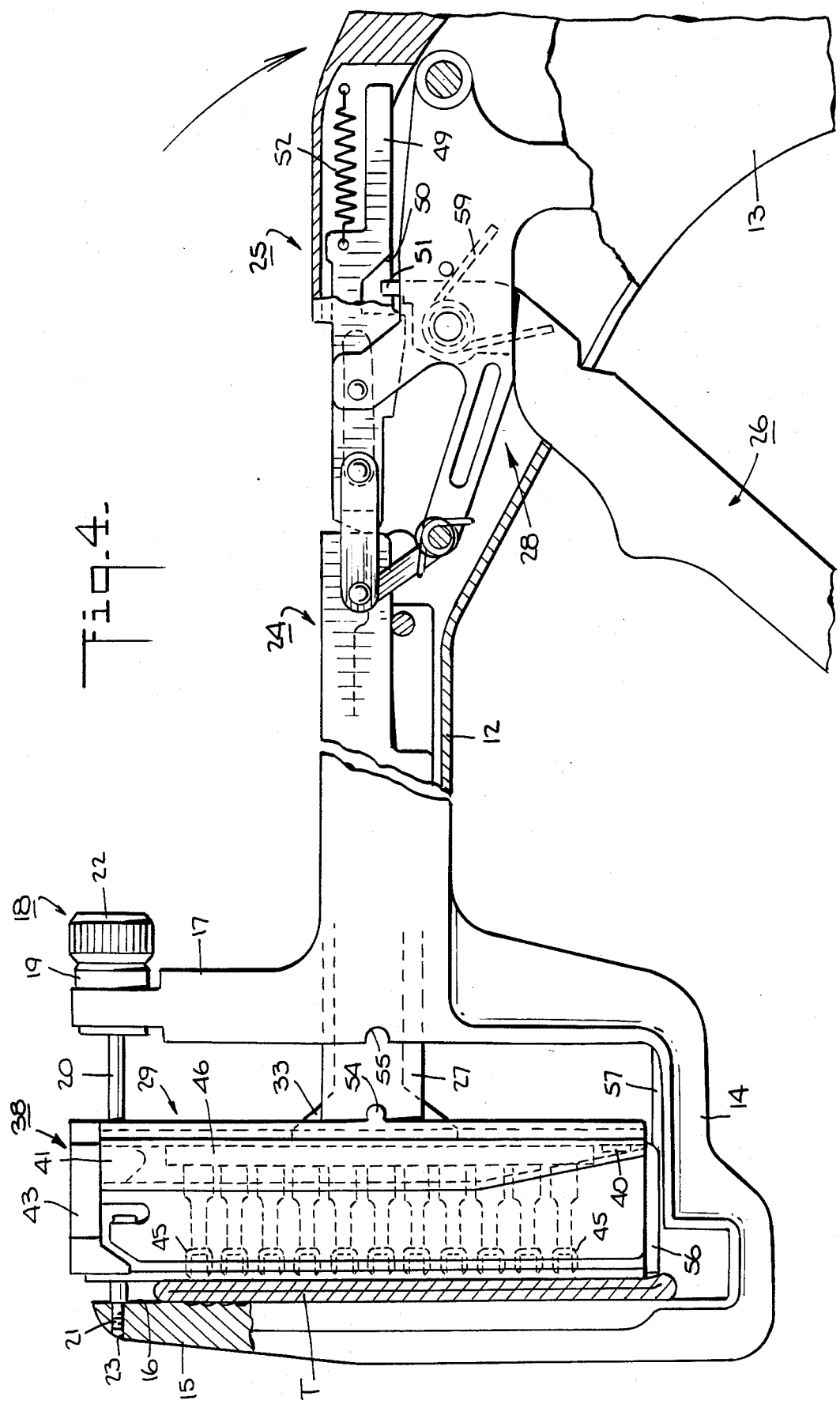
FIG. 4 illustrates the instrument of FIG. 1 in a state wherein the tissue has been initially clamped.

Referring to FIGS. 3 and 7, the second or proximal actuator means 25 is constructed in similar manner to that as described in U.S. Pat. No. 4,383,634 FIGS. 3 and 14. In this regard, the proximal actuator means 25 is articulated to the joint 28 at the distal end in order to pivot between an opened position as shown in FIG. 3 and a closed position as shown in FIG. 4. To this end, the proximal actuator means 25 includes a curved portion 47 which is provided with knurling 48 at the proximal end for gripping purposes. As is known, the second actuator means 25 is articulated for reciprocating the distal actuator means 24, as indicated in FIG. 3, so that when the proximal actuator means 25 pivots from the open position to the closed position, the distal actuator means 24 slides forwardly. In addition, the second actuator means 25 has a plunger 49 provided with a recess 50 to receive a detent 51 of the handle 26 to move forwardly when the handle 26 is pivoted clockwise as viewed in FIG. 4. In addition, a suitable spring 52 is provided to bias the plunger 49 in the proximal direction. When pushed forwardly, the plunger 49 abuts the plunger rod 30 of the distal actuator means in order to pushe the plunger rod 30 forwardly.

Of note, the articulated joint 28 between the actuator means 24, 25 and the handle 26 is of generally known construction, for example, as described in U.S. Pat. No. 4,383,634. In addition, a suitable safety latch 53 is provided in the frame 11 to prevent accidental pivoting of the handle 26.

Referring to FIG. 1, a retaining means is provided for retaining the distal actuator means 24 in the frame 11 when in the closed position in order to prevent movement of the actuator means 24 to the open position. As illustrated, the retaining means includes a pin 54 which is integrally connected to the bar 27 of the actuator means 24 adjacent to the cartridge holder 29 as well as a recess 55 in one side of the bar 27. When the distal actuator means 24 is pivoted from the open position shown in FIG. 7 into the closed position, as indicated in FIG. 3, the distal end of the bar 27 is manipulated so that the pin 54 is seated within the recess 55. In this regard, as the bar 27 is moved toward the closed position, the cartridge holder 29 can be manually grasped so that the pin 54 passes freely over the cleft 17 and is positioned in front of the recess 55. Thereafter, a slight movement of the cartridge holder 29 and bar 27 in the proximal direction is able to seat the pin 54 within the recess 55. During pivoting of the bar 27, the pin 34 enters the recesses 35 in the frame 11.

Once the pin 54 is seated in the recess 55, the distal actuator means 24 cannot be readily pivoted into the open position. At the same time, placement of the pin 54 in the recess 55 aligns the cartridge holder 29 relative to the anvil 16. Thus, when a cartridge 38 is slid into the holder 29, the cartridge is also aligned with the anvil 16.

Referring to FIG. 6, the stapling cartridge 38 is provided, in known manner, with a pair of outwardly extending flanges 56 at the forward end which cooperate with a rail 57 on the U-shaped extension 14 of the frame 11 such that the flanges center the cartridge 38 on the rail 57. In addition, the flanges 56 and rail 57 serve to guide the cartridge 38 during a stapling operation.

In using the instrument 10, the distal actuator means 24 is placed in the closed position with the pin 54 in the recess 55 as indicated in FIG. 3. At the same time, a stapling cartridge 38 is slid into the arms of the holder 29 with the flanges 58 engaging against the sides of the rail 59 of the frame 11. In this position, the cartridge 38 is aligned with the anvil 16. After tissue T has been placed between the cartridge 38 and the anvil 16, the alignment and guide pin unit 18 is fitted into place. At this time, the pin 20 is passed through a passage 58 at the rear end of the cartridge 38 and threaded into the threaded aperture 23 in the distal leg 15 of the frame extension 14. Thereafter, the cartridge 38 can be guided by the rail 57 and the pin 20.

Next, as indicated in FIG. 4, the proximal actuator means 25 is pivoted from the open position of FIG. 3 into the closed position. This causes the forward movement of the first actuator means 24 including the cartridge holder 29 and the cartridge 38. At this time, the tissue to be stapled is clamped between the distal side of the cartridge 38 and the anvil 16.

Figure 5:
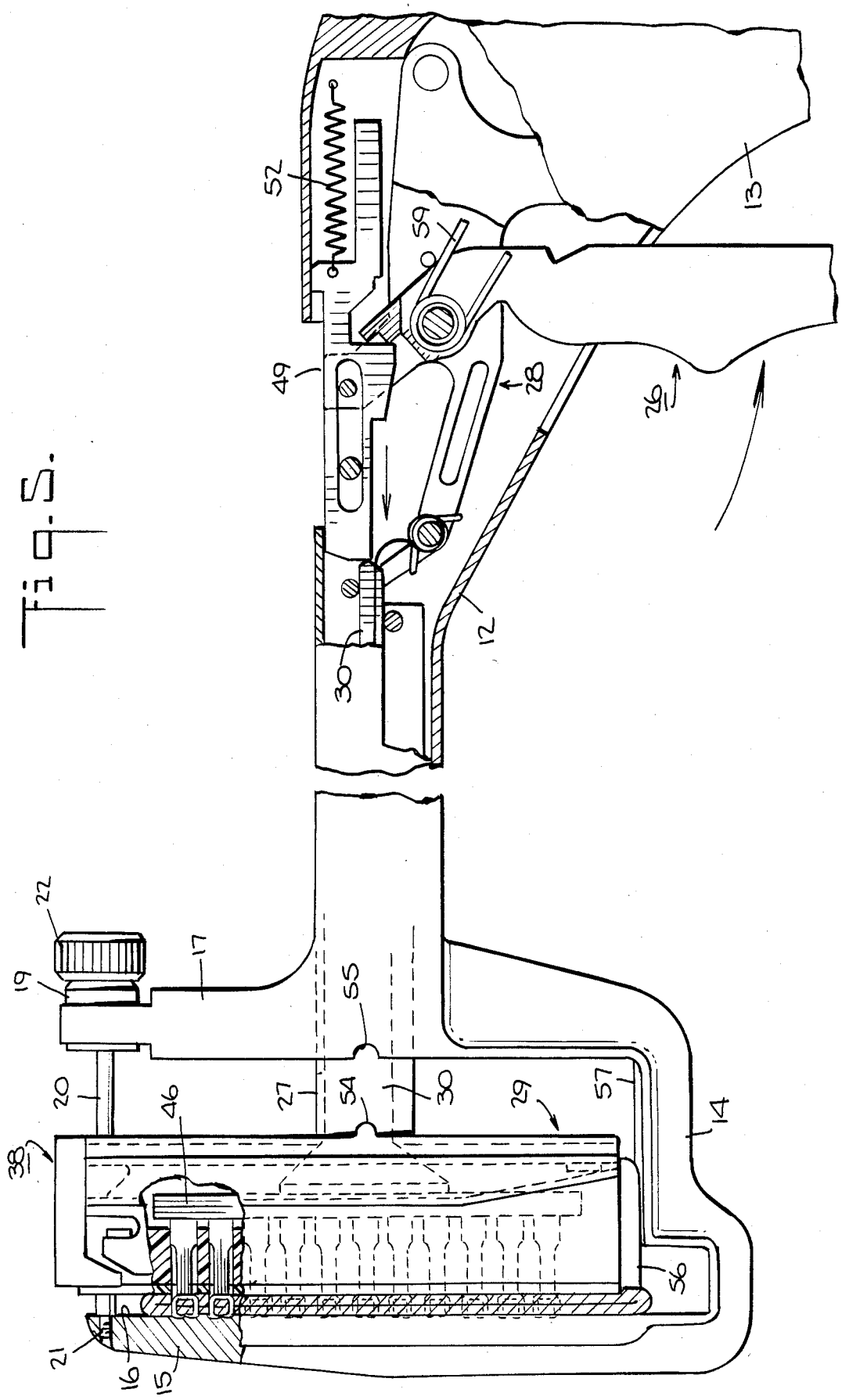
FIG. 5 illustrates the instrument of FIG. 1 in a state in which the tissue has been stapled.

Next, with the safety latch 53 released, the handle 26 is pivoted counter-clockwise as indicated in FIG. 5 so that the plunger rod 30 is moved into the cartridge housing 39 to push the staples 45 outwardly through the tissue T and against the anvil 16 for clinching in known manner.

Thereafter, the handle 26 is released and returned via a spring 59 to the initial position. The proximal actuator means 25 is then pivoted into the open position shown in FIG. 3, the alignment pin 20 is unthreaded from the distal leg 15 and retracted, and the instrument 10 removed fromt he patient. At that time, the emptied cartridge 38 can be disposed of and the instruction 10 subjected to cleaning.

For cleaning purposes, the second actuator means 25 is disposed in the open position and the distal actuator means 24 manipulated forwardly so as to remove the pin 54 from the recess 55 so that the actuator means 24 can be moved to the open position for cleaning purposes.

Referring to FIG. 2, the tissue T which has been stapled has a seam 60 which is formed by the four parallel rows of staples 45 in a pattern so as to prevent the passage of blood through the seam 60. For example, if a stream of blood were moving from the left-hand side of the seam 60 towards the right-hand side, the stream would initially pass between two staples 45 in the first row. Upon reaching the facing staple in the second row, the stream would divert, for example upwardly as viewed in FIG. 2. Upon reaching the next gap, the blood would tend to pass through until reaching a staple in the third row. The blood stream would again be diverted upwardly or downwardly, as viewed inFIG. 2, until reaching the next gap. Because of the contorted path which the blood stream would have to follow through the seam 60, it has been found that the blood does not bleed through as may be the case if there were only two rows of staples.

The invention thus provides a technique for forming stapled seams in tissue in a manner to resist disruption. In this regard, the surgical instrument is able to form a seam of four parallel equispaced rows of surgical staples. In the event that disruption takes place of one row via a zipper effect, the remaining three rows of staples provide a secure seam. Further, since the four rows of staples can be ejected by a single instrument, the overall time required to form the seam is reduced as compared with previously known techniques.

In addition, the invention provides a stapling instrument in which a disposable cartridge can be inserted and aligned in a relatively simple manner relative to an anvil.

Still further, the invention provides an instrument which can be readily cleaned without being disassembled.

The invention further provides a surgical stapling instrument which has an integrated disposable cartridge holder which permits easy alignment of a stapling cartridge while also facilitating cleaning of the cartridge holder with the instrument.

What is claimed is:

1. A surgical stapling instrument comprising
   a frame having an anvil disposed at a distal end;
   a first actuator means connected at a proximal end to said frame for movement between a closed position coaxial with said frame and an open position away from said frame to permit cleaning of said frame and said actuator means, said actuator means being reciprocally mounted within said frame when in said closed position;
   a stapling cartridge holder integrally mounted on a distal end of said actuator means; and
   a second actuator means connected to said frame and said first actuator means for movement between an open position away from said frame and a closed position within said frame for reciprocating said first actuator means within said frame when in said closed position thereof.

2. A surgical stapling instrument as set forth in claim 1 further comprising retaining means for retaining said first actuator means in said frame in said closed position thereof to prevent movement of said first actuator means to said open position thereof.

3. A surgical stapling instrument as set forth in claim 2 wherein said retaining means includes a pin on said first actuator means adjacent said cartridge holder and a recess in said frame receiving said pin therein.

4. A surgical stapling instrument as set forth in claim 1 which further comprises
   a plunger rod reciprocally mounted in said first actuator means for expelling staples from a cartridge mounted in said holder and being aligned with said second actuator means;
   a handle pivotally mounted in said frame for moving said second actuator means against said plunger rod to expel staples from a cartridge in said holder against said anvil.

5. In combination,
   a surgical stapling instrument including a frame having an anvil disposed at a distal end, a first actuator means reciprocally mounted in said frame and having a stapling cartridge holder integrally mounted at a distal end opposite said anvil, said first actuator means being connected at a proximal end to said frame for movement between a closed position coaxial with said frame and an open position away from said frame to permit cleaning of said frame and said actuator means, and a means mounted in said frame for moving said first actuator means towards said anvil; and
   a stapling cartridge removably mounted in said holder, said cartridge including a housing having four parallel rows of apertures on a distal side in facing alignment with said anvil, said rows being arranged in closely spaced staggered relation to each other, a plurality of staples in said housing and means within said housing for moving said staples simultaneously from said housing through said apertures and against said anvil.

6. The combination as set forth in claim 5 wherein said instrument includes a plunger rod slidably mounted in said first actuator means and aligned with an opening in said housing of said cartridge and a handle pivotally mounted in said frame for pushing said rod into said housing to expel said staples therefrom.

7. The combination as set forth in claim 5 which further includes a pin on said first actuator means adjacent said cartridge holder and a recess in said frame receiving said pin therein to prevent movement of said first actuator means to said open position thereof.

8. The combination as set forth in claim 5 wherein said rows of apertures are disposed on a centerline-to-centerline spacing of 0.08 inches.

* * * * *

UNITED STATES PATENT AND TRADEMARK OFFICE
CERTIFICATE OF CORRECTION

PATENT NO. : 4,802,614

DATED : February 7, 1989

INVENTOR(S) : DAVID T. GREEN

It is certified that error appears in the above-identified patent and that said Letters Patent is hereby corrected as shown below:

Title page:

In the Abstract, line 2 "holders" should be -holder-
Column 1, line 13 "cartridges" should be -cartridge-
Column 1, line 15 "elements" should be -element-
Column 5, line 26 "pushe" should be -push-
Column 6, line 30 "fromt he" should be -from the-
Column 6, line 31 "instruction" should be -instrument- Signed and Sealed this Twenty-third Day of January, 1990

Attest:

JEFFREY M. SAMUELS

Attesting Officer    Acting Commissioner of Patents and Trademarks